(12) United States Patent
Kutzko et al.

(10) Patent No.: US 6,581,606 B2
(45) Date of Patent: *Jun. 24, 2003

(54) METHOD, APPARATUS AND SYSTEM FOR USE IN TREATING PATIENT WITH A DRUG HAVING AN ANTINEOPLASTIC EFFECT TO OPTIMIZE THERAPY AND PREVENT AN ADVERSE DRUG RESPONSE

(75) Inventors: John D. Kutzko, Nokomis, FL (US); John P. McMichael, Wexford, PA (US); Michaeal G. Singer, Harrisville, MI (US)

(73) Assignee: The Rx Files Corporation, Nokomis, FL (US)

( * ) Notice: Subject to any disclaimer, the term of this patent is extended or adjusted under 35 U.S.C. 154(b) by 110 days.

This patent is subject to a terminal disclaimer.

(21) Appl. No.: 09/817,906

(22) Filed: Mar. 26, 2001

(65) Prior Publication Data

US 2001/0018919 A1 Sep. 6, 2001

Related U.S. Application Data

(63) Continuation-in-part of application No. 09/348,592, filed on Jul. 6, 1999, now Pat. No. 6,267,116, and a continuation-in-part of application No. 09/644,503, filed on Aug. 24, 2000.

(51) Int. Cl.$^7$ .............................................. A61B 19/00
(52) U.S. Cl. ..................................... 128/898; 600/300
(58) Field of Search .................... 128/897–98; 600/300, 600/308, 347, 364–66, 368

(56) References Cited

U.S. PATENT DOCUMENTS 6,267,116 B1 * 7/2001 McMichael ................. 128/898

* cited by examiner

*Primary Examiner*—John P. Lacyk
(74) *Attorney, Agent, or Firm*—Gifford, Krass, Groh, Sprinkle, Anderson & Citkowski, P.C.

(57) ABSTRACT

A method, apparatus and system for use in treating a patient receiving an antineoplastic drug to optimize therapy and prevent an adverse drug response. This system employs surrogate markers or indicators including blood levels of the antineoplastic drug to determine the next required dose for a patient. Since the surrogate markers are employed as a percent change in status, virtually any indicator can be used. Surrogate markers could include any measure of the effectiveness of the antineoplastic drug's action. Given the effectiveness of the antineoplastic drug's action relative to the surrogate markers, a change in antineoplastic drug dose is calculated by the system. Conversely, by employing this system, one could determine the expected result of the antineoplastic drug dose change on the surrogate markers.

20 Claims, 2 Drawing Sheets

METHOD, APPARATUS AND SYSTEM FOR USE IN TREATING PATIENT WITH A DRUG HAVING AN ANTINEOPLASTIC EFFECT TO OPTIMIZE THERAPY AND PREVENT AN ADVERSE DRUG RESPONSE

RELATED APPLICATIONS

The present patent application is a continuation-in-part of U.S. patent application Ser. No. 09/348,592 filed on Jul. 6, 1999, now U.S. Pat. No. 6,267,116 and of U.S. patent application Ser. No. 09/644,503 filed on Aug. 24, 2000, pending the entire contents of both of which applications are incorporated herein by reference thereto.

This document may contain material which is the subject of copyright protection. All rights in such copyrightable material are hereby reserved.

FIELD OF THE INVENTION

The present invention relates generally to a method, apparatus and system for use in treating a patient with an antineoplastic drug to optimize drug therapy and to prevent an adverse drug response.

The present invention can utilize either drug levels or other surrogate markers to determine the effectiveness of the dosing regimen and, if necessary, to suggest a new more optimal drug dose.

The term "antineoplastic drug" as used herein includes, but is not limited to: chemotherapeutic agents; drugs which have an antineoplastic effect, but which are not normally classified as chemotherapeutic agents, such as, for example, warfarin, heparin, minocycline, Vioxx, Celebrex, etc.; drugs which have an antineoplastic effect that are currently in Phase I, II and/or III trials; epothilones, analogs of epothilones, and their class of compounds; melphalan (Alkeran), carmustine {BCNU} (BiCNU), busulfan (Busulfex), lomustine {CCNU} (CeeNU), cyclophosphamide (Cytoxan), dacarbazine (DTIC-Dome), polifeprosan 20 with carmustine implant (Giladel), sterile ifosfamide (Ifex), chlorambucil (Leukeran), mechlorethamine (Mustargen), busulfan (Myleran), cyclophosphamide (Neosar), carboplatin (Paraplatin), cisplatin (Platinol), thiotepa (Thioplex), capecitabine (Xeloda), streptozocin (Zanosar), bicalutamide (Casodex), flutamide (Eulexin), leuprolide acetate (Lupron), nilutamide (Nilandron), leuprolide acetate (Viadur), doxorubicin hydrochloride (Adriamycin), bleomycin sulfate (Blenoxane), daunorubicin hydrochloride (Cerubidine), dactinomycin (Cosmegen), daunorubicin citrate liposome injection (DaunoXome), doxorubicin hydrochloride liposome injection (Doxil), epirubicin hydrochloride (Ellence), idarubicin hydrochloride (Idamycin), mitomycin (Mutamycin) doxorubicin (Rubex), valrubicin (Valstar), anastrozole (Arimidex), toremifene citrate (nolvadex), fluorouracil (Adrucil), cytarabine (Cyttosar-U), fluorouracil (Efudex), fludarabine (Fludara), (Fluorouracil), floxuridine (FUDR), interferon alfa-$2b$, recombinant (Intron A), Immunex (Methotrexate), plicamycin (Mithracin), mercaptopurine (Purinethol), methotrexate (Rheumatrex), interferon alfa-$2a$, recombinant (Roferon-A (Thioguanine), medroxyprogersterone acetate (Depo-Provera), estramustine phosphate sodium (Emcyt), estradiol (Estrace), leuprolide acetate (Lupron), megestrol acetate (Megace), octreotide acetate (Sandostatin), octreotide acetate for injection suspension (Sandostatin LAR), deithylstilbestrol diphosphate (Stilphostrol), testolactone (Teslac), goserelin acetate (Zoladex), etoposide phosphate (Etopophos), vincristine sulfate (Oncovin), etoposide (Toposar), vinblastine (Velban), etoposide (VePesid), vincristine sulfate (Vincasar PFS), teniposide (Vumon), trastuzumab (Herceptin), gemtuzumab ozogamicin (Mylotarg), rituximab (Rituxan), exemestane (Aromasin), irinotecan hydrocholride (Camptosar), asparaginase (Elspar), gemcitabine hydrochloride (Gemzar), altretamine (Hexalen), topotecan hydrochloride (Hycamtin), hydroxyurea (Hydrea), (Leucovorin calcium), cladribine (Leustatin), mitotane (Lysodren), procarbazine hydrochloride, (Matulane), vinorelbine tartrate (Navelbine), pentrostatin sodium (Nipent), mitoxantrone (Novantrone), pegaspargase (Oncaspar), denileukin diftitix (Ontak), altretinoin (Panretin), porfimer (Photofrin), bexarotene (Targretin), bexarotene (Targretin Gel), paclitaxel (Taxol), docetaxel (Taxotere), temozolomide (Temodar), bacillus of Calmette and Guerin (Theracys BCG Live), arsenic trioxide (Trisenox), tretinoin (Vesanoid); substances which foster anti-tumor activity; and all substances derived from and/or related to the foregoing substances.

Furthermore, wherever the generic term "antineoplastic drug" is used herein it is also intended to mean species which employ any or several of the individual antineoplastic drugs as defined and/or alluded to hereinabove.

BACKGROUND OF THE INVENTION

When a patient begins taking an antineoplastic drug or any medication for a length of time, a titration of the amount of drug taken by the patient is necessary in order to achieve the optimal benefit of the drug, and at the same time to prevent any undesirable side effects that taking too much of the drug could produce. Thus, there is a continuous balance between taking enough drug in order to gain the benefits from that drug and at the same time not taking so much drug as to illicit a toxic event.

There is large inter-individual variability in the patient pharmocodynamic and pharmacokinetic interactions of drugs. What may be an appropriate drug dose for one individual, may be too much or too little for another. Prior to this invention a physician was required to estimate the correct drug dosage for a patient and then to experiment with that dosage, usually by trial and error, until the correct dosage was achieved. Likewise, the FDA labeling of a drug suggests dosages based on epidemiological studies and again does not account for inter-individual variability. Non-linear least squares modeling methods involve the use of large amounts of data relating to a general population in order to calculate a best fit. Much like linear regression models, this method cannot take into account the variability between people with the same population characteristics.

Bayesian analysis is another method used to relate drug dose to efficacy. This method employs large-scale population parameters to stratify a population in order to better characterize the individuals. This method does not take into account the changes that can occur within a person over time, and as a result cannot reliably estimate dosages.

Pharmacokinetic compartment modeling has had success with some drugs, but because the models are static and cannot adapt themselves to changes within a population or a patient, they are once again undesirable for dynamically determining drug dosages.

Expert systems have been developed using technology to predict drug dosages for immunosuppressant drugs (see, e.g., U.S. Pat. Nos. 5,365,948, 5,542,436 and 5,694,950). These algorithms, however, are not generic and only use immunosuppressant blood levels. Each algorithm is specific to an individual immunosuppressant drug. As it stands, these prior inventions cannot be applied to other drugs and do not have a non-linear feedback loop mechanism.

It is a desideratum of the present invention to avoid the animadversions and limitations of prior systems.

SUMMARY OF THE INVENTION

The present invention provides a method for calculating a revised dose of an antineoplastic drug for a patient using said antineoplastic drug, comprising the steps of: accepting as a first input the patient's current antineoplastic drug dose; accepting as a second input a maximum dose of the antineoplastic drug; accepting as a third input a percent response of the patient based on one or more surrogate markers used to monitor said antineoplastic drug; and determining a revised dose, wherein said revised dose is a function of said current dose minus a ratio of the percent response of the patient and a ratio of said current dose to said maximum dose plus the percent of individual patient response multiplied by a response factor.

The present invention also provides a storage device having stored thereon an ordered set of instructions which, when executed by a computer, performs a predetermined method, comprising: first means for accepting as input a patient's current antineoplastic drug dose; second means for accepting as input a maximum dose of the antineoplastic drug; third means for accepting as input a percent response of a patient based on surrogate markers for monitoring said antineoplastic drug; and fourth means for calculating a revised dose, wherein said revised dose is a function of said current dose minus the ratio of a percent response of the patient and the ratio of said current dose to said maximum dose plus the percent of individual patient response multiplied by a response factor.

The present invention also provides an apparatus for calculating a revised dose of an antineoplastic drug for a patient, comprising: first means for accepting as input one or more markers which indicate a patient's response to a dose of said antineoplastic drug; second means for accepting as input the patient's current antineoplastic drug dose; third means for accepting as input the maximum dose of the antineoplastic drug; and fourth means for calculating a revised dose of the antineoplastic drug as a function of said markers, said current antineoplastic drug dose, and said maximum antineoplastic drug dose.

DETAILED DESCRIPTION OF THE INVENTION

The present invention provides a method and system for use in treating a patient receiving an antineoplastic drug to optimize therapy and prevent an adverse drug response. This system employs surrogate markers or indicators including blood levels of the antineoplastic drug to determine the next required dose for a patient. Since the surrogate markers are employed as a percent change in status, virtually any indicator can be used. Surrogate markers could include any measure of the effectiveness of the antineoplastic drug's action. Given the effectiveness of the antineoplastic drug's action relative to the surrogate markers, a change in antineoplastic drug dose is calculated by the system. Conversely, by employing this system, one could determine the expected result of the antineoplastic drug dose change on the surrogate markers.

Figure 1:
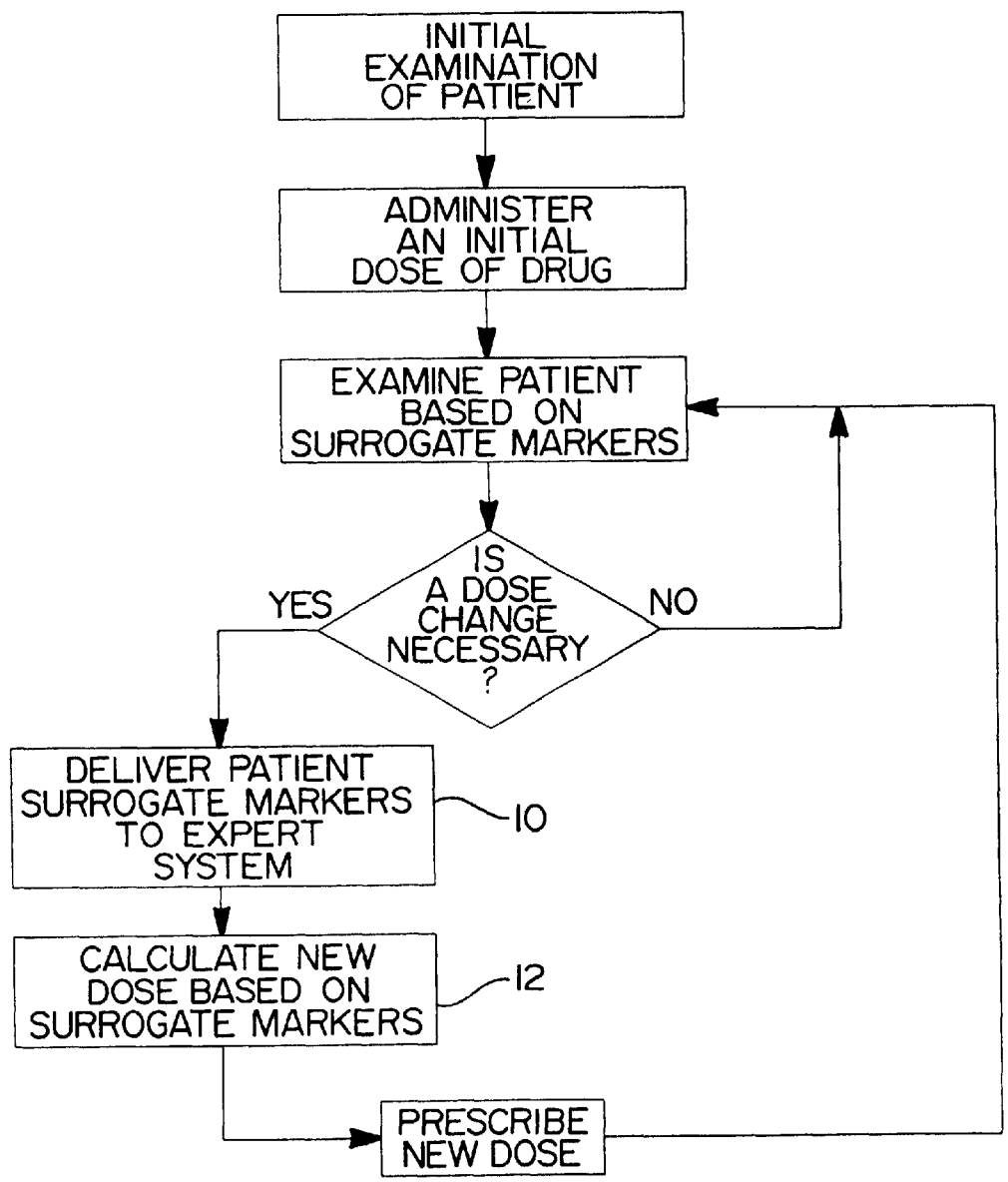
FIG. 1 shows a flow chart of the process by which revised doses of an antineoplastic drug are determined, according to the method of the invention described herein.

According to the present invention, patient dosing occurs through a cyclic series of events, depicted in flow chart form in FIG. 1. After an initial examination, an initial dose of an antineoplastic drug is prescribed and administered by a physician for a patient. The initial dose is based on the FDA recommended dosage found on the drug label. The antineoplastic drug dose is further refined upon repeated dosing by the physician based on the patient's response to the antineoplastic drug. Too much antineoplastic drug could cause the patient to experience toxic antineoplastic drug effects, and the antineoplastic drug dose would need to be reduced. Too little antineoplastic drug could cause the patient not to receive the benefit the antineoplastic drug therapy could offer, and the dosage would need to be increased.

The preferred embodiment of the invention requires that a physician determine the percentage of response by the patient to the antineoplastic drug based on the surrogate markers for that antineoplastic drug. A relationship is then employed which uses the input parameters described herein to determine the next dose for the patient.

Each specie of the invention has two preferred embodiments; one which uses actual numerical surrogate markers to calculate a dose, and another embodiment that uses percentages as the numerical input for the surrogate markers.

A method of this invention for use in treating a patient receiving an antineoplastic drug to optimize therapy and to prevent an adverse antineoplastic drug response can be implemented in two different embodiments, two of which will each be described separately.

FIG. 1 shows a flow chart of the overall process of treating a patient using this expert system. The actual expert system, however, performs only the steps shown in blocks 10 and 12 of the flow chart.

Figure 2:
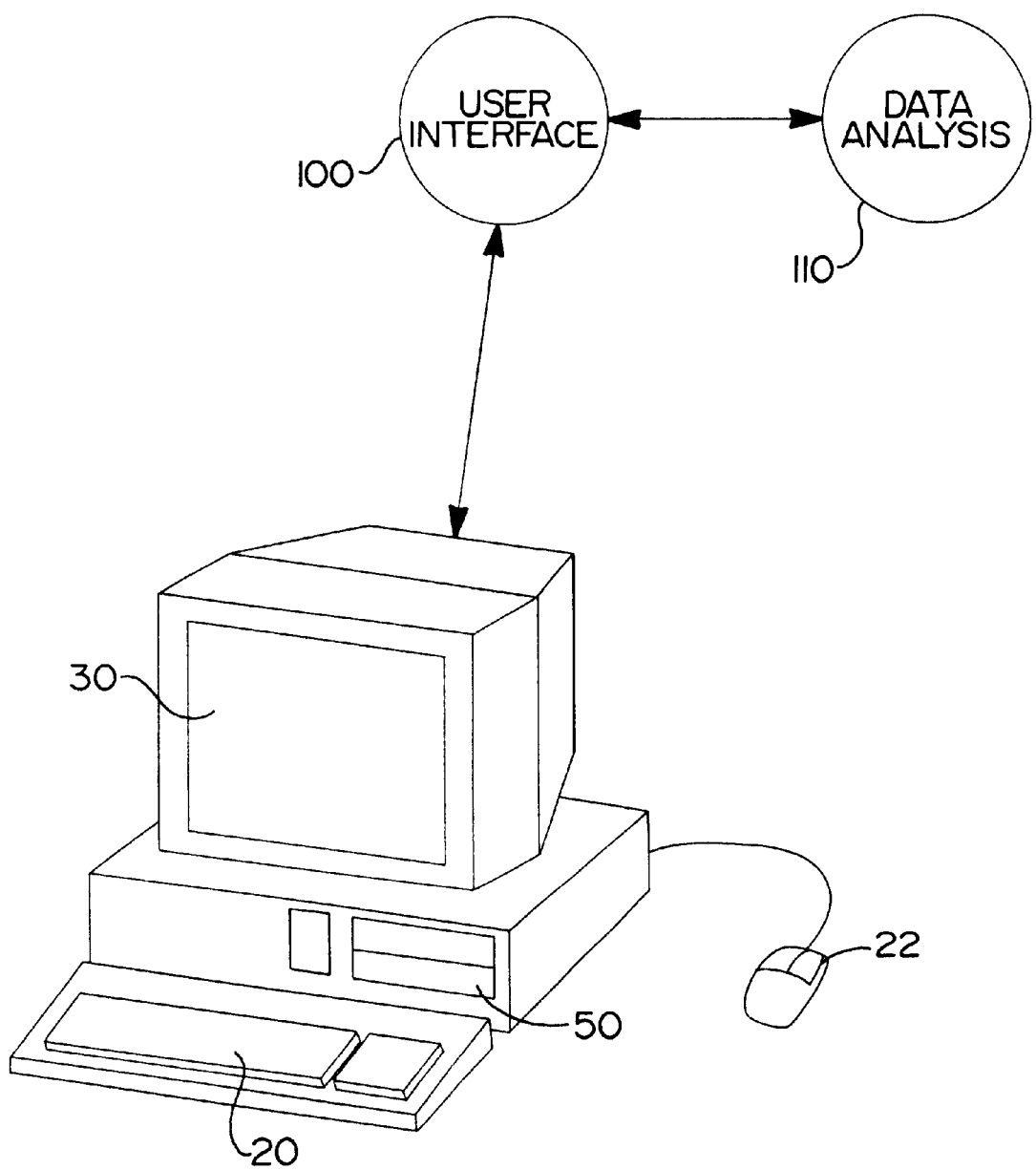
FIG. 2 shows an apparatus for use in calculating revised doses of an antineoplastic drug according to the present invention.

This expert system includes a general purpose computer, shown in FIG. 2, comprising an input means, preferably a keyboard 20 and/or a mouse 22, an output means 30, preferably a video display screen, a data storage means 50, preferably a hard disk drive, and a processor. The expert computer program receives input data from a physician regarding the patient's current antineoplastic drug dose, the maximal dose range for the antineoplastic drug, and the percent response of the patient based on the surrogate markers used to monitor the antineoplastic drug. Also characterized is the patient's response to the last dosing cycle as well as a dose response constant.

This allows the expert system to individualize the patient dosing based on the patient's individual response to the antineoplastic drug. The system calculates a revised dosage based on the data input by the physician. The software portion of the invention includes a user interface portion 100 to receive the input data and to output the revised dosage information, and a data analysis portion 110, which calculates the new dosage information based on the input data.

Numerical Surrogate Markers Embodiment

A physician prescribes an antineoplastic drug for a patient based on the FDA recommended dose on the label of the antineoplastic drug. The physician then re-evaluates the patient, usually daily, either in person or remotely depending on the agent being prescribed. During the subsequent evaluations by the physician, the surrogate markers are monitored and sequentially compared to determine if there are any toxicities associated with the antineoplastic drug.

Also the numerical markers will evaluated to see if the desired effect of the antineoplastic drug is being achieved. Based on this evaluation by the physician, the current antineoplastic drug dose, the current antineoplastic drug numerical marker, the desired antineoplastic drug numerical marker, and the previous antineoplastic drug numerical marker are then input into the embodiment and the new antineoplastic drug dose is calculated based on the equation:

$$NAD=CAD-\{[<(CANM-DANM)/CANM>/>1+(CAD/HIGH)>]\times CAD\}+LV$$

where:

$$LV=\{(RESP\times CAD)\times[(1+D)-(1+E)]/\text{abs }(1+D)\}/[1.3\hat{\ }(CAD/HIGH)]$$

$$E=CANM-PANM$$

$$D=(DANM-PANM)$$

$$RESP=RESPONSE/100$$

and wherein:

NAD=New Antineoplastic drug Dose
CAD=Current Antineoplastic drug Dose
CANM=Current Antineoplastic drug Numerical Marker
DANM=Desired Antineoplastic drug Numerical Marker
PANM=Previous Antineoplastic drug Numerical Marker
HIGH=The input parameter that is the high dose range for said antineoplastic drug
RESPONSE=Total dose available for individualizing patient dose
abs=The absolute value of
^=Raised to the nth power.

Percentage Surrogate Markers Embodiment

In this preferred embodiment, a physician prescribes an antineoplastic drug for a patient based on the FDA recommended dose on the label of the antineoplastic drug. The physician then re-evaluates the patient, usually daily, either in person or remotely depending on the agent being prescribed. During the subsequent evaluations by the physician, the surrogate markers are monitored and sequentially compared to determine if there are any toxicities associated with the antineoplastic drug. Also the surrogate markers are evaluated to see if the desired effect of the antineoplastic drug is being achieved.

Based on this evaluation by the physician, the current antineoplastic drug dose, and the percent response of the patient to the last dosing based on a surrogate marker are then input into the system and the new antineoplastic drug dose is calculated based on the equation:

$$NAD=CAD-\{[<(SMP-100)/SMP>/<1+(CAD/HIGH)>]\times CAD\}+LV$$

where:

$$LV=\{(RESP\times CAD)\times[(100-RES)\times0.01]\}/[1.3\hat{\ }(CAD/HIGH)]$$

$$RESP=RESPONSE/100$$

and wherein:

NAD=New Antineoplastic drug Dose
CAD=Current Antineoplastic drug Dose
SMP=Surrogate Marker Percent response of patient
RES=Percent response of patient to last dosing based on surrogate marker
HIGH=The input Parameter that is the high dose range for said antineoplastic drug
RESPONSE=Total dose available for individualizing patient dose
^=Raised to the $n^{th}$ power.

This cycle of repeated re-evaluation of the numerical surrogate markers is continued as long as the patient is required to take the antineoplastic drug.

Two general embodiments of the invention have been described, one using numerical markers, and one using a percentage surrogate marker.

Some specific examples are set forth hereinbelow.

EXAMPLE I

A current dose of Gemzar (gemcitabine) is 1500 mg. The platelet count is 46,000/mm3 and this patient is recognized as having a Grade III toxicity as defined by the National Cancer Institute (NCI) Common Toxicity Criteria. The current practice would be to delay the course of treatment by not administering any chemotherapeutic to the patient until his/her platelet count has risen, on its own or by way of another pharmacological agent used to increase platelet count, to a Grade II toxicity of 50,000–75,000/mm3 or a Grade I toxicity of >75,000/mm3.

The present invention allows for calculation of a dose with regard the dose of a chemotherapeutic necessary to positive impact a negative surrogate marker. In this case, the prescriber would use the following information for the patient receiving Gemzar: Current Dose 1500 mg; Current Marker 46,000 (a unitless marker indicative of the current platelet count); Desired Marker 75,000 (a unitless marker indicative of where the prescriber wants to see the platelet count raised to); Previous marker (a unitless marker that may or may not be used due to availability that is indicative of the patient's previous amount of measured surrogate marker).

The New Dose calculation would give a recommended dose of 849.86 mg. The Unit Dose would recommend 840 mg because this is the most accurate measurement that can be made due to the incremental doses sold by the pharmaceutical manufacturer. The Expected Marker would be 75,440/mm3; this is what is expected to be actually seen in the patient with regard to the difference in amount of drug recommended as measurable in Expected Dose to New Dose.

EXAMPLE II

A current dose of Taxol (paclitaxel) is 375 mg. The absolute neutrophil count (ANC) is 660/mm3 and this patient is recognized as having a Grade III toxicity as defined by the NCI Common Toxicity Criteria. The current practice would be to delay the course of treatment by not administering any chemotherapeutic to the patient until his/her ANC has risen, on its own or by way of the administration of another pharmacological agent used to increase the ANC, to a Grade II toxicity of 1,000–1,500/mm3 or Grade I toxicity of 1,500–2,000/mm3.

The present invention allows for calculation of a dose of a chemotherapeutic with regard to the dose necessary to positively impact a negative surrogate marker. In this case, the prescriber would use the following information for the patient receiving Taxol: Current Dose 375 mg; Current Marker 660 (a unitless marker indicative of the current platelet count); Desired Marker 1,200 (a unitless marker indicative of where the prescriber wants to see the platelet count raised to); Previous Marker 640 (a unitless marker indicative of the patient's previous ANC).

The New Dose calculation would give a recommended dose of 187.5 mg. The Unit Dose would recommend 186 mg because this is the most accurate measurement that can be made due to the incremental doses sold by the pharmaceutical manufacturer. The Expected Marker would be 1,242.1/mm3; this is what is expected to be actually seen in the patient with regard to the difference in amount of drug recommended as measurable in Expected Dose to New Dose.

EXAMPLE III

A current dose of Xeloda (capecitabine) is 3700 mg. The surrogate marker being used is Palmar-Plantar Eryhtrodyesthesia or Hand-Foot Syndrome (HFS), and this patient is recognized as having a Grade III toxicity as defined by the NCI Common Toxicity Criteria as having the following characteristics; blistering, ulceration, or swelling interfering with walking or normal daily activities; cannot wear regular clothing. The current practice is to interrupt therapy until HFS is resolved to Grade 0–1 with a dosage adjustment of 75% of the starting dose for the resumption of treatment. Grade I toxicity is defined as mild erythrema swelling, or desquamation not interfering with daily activities.

The present invention allows for calculation of a dose of a chemotherapeutic with regard to lowering the dose necessary to positively impact the HFS toxicity rating scale. In this case, the prescriber would use the following information for the patient receiving Xeloda (capecitabine): Current Dose 3700 mg; Current Marker 3 (a unitless marker indicative of the Grade III toxicity present in the patient); Desired Marker 1 (a unitless marker indicative of where the prescriber wants to see the Grade III toxicity lowered to); Previous Marker (a unitless marker indicative of the patient's previous HFS toxicity grading).

The New Dose calculation would give a recommended dose of 2214.7 mg. The Unit Dose would recommend 2250 mg because this is the most accurate measurement that can be made due to the incremental doses sold by the pharmaceutical manufacturer. The Expected Marker would be 1.0475, and would be difficult to discern due to the subjective nature of the surrogate marker measured. When the ability of the prescriber to weight a subjective measurement is determined and the corresponding subjective measurement could be metered into fractional units, this is what is expected to be actually seen in the patient with regard to the difference in amount of drug recommended as measurable in Expected Dose to New Dose.

Although the invention has been described in detail in the foregoing for the purpose of illustration, it is to be understood that such detail is solely for that purpose and that variations can be made therein by those of ordinary skill in the art without departing from the spirit and scope of the invention as defined by the following claims, including all equivalents thereof.

What is claimed is:

1. A method for calculating a revised dose of an antineoplastic drug for a patient using said antineoplastic drug, comprising the steps of:

accepting as a first input the patient's current antineoplastic drug dose;

accepting as a second input a maximum dose of the antineoplastic drug;

accepting as a third input a percent response of the patient based on one or more surrogate markers used to monitor said antineoplastic drug; and determining a revised dose, wherein said revised dose is a function of said current dose minus a ratio of the percent response of the patient and a ratio of said current dose to said maximum dose plus the percent of individual patient response multiplied by a response factor.

2. The method of claim 1, wherein:

said determining step includes determining said revised dose based on the equation $$RAD = CAD - \{[<(SMP-100)/SMP>/<1+(CAD/HIGH)>] \times CAD\} + LV$$

where:

$$LV = \{(RESP \times CAD) \times [(100-RES) \times 0.01]\}[1.3^{\wedge}(CAD/HIGH)]$$

RESP=RESPONSE/100; and wherein:

RAD=revised antineoplastic drug dose

CAD=current antineoplastic drug dose

SMP=surrogate marker percent response of patient

RES=percent response of patient to last dosing based on surrogate marker

HIGH=the input parameter that is the high dose range for said antineoplastic drug RESPONSE=total dose available for individualizing patient dose abs=the absolute value of ^=raised to the $n^{th}$ power.

3. The method of claim 1, wherein: said antineoplastic drug is selected from a group comprising: chemotherapeutic agents; drugs which have an antineoplastic effect, but which are not normally classified as chemotherapeutic agents including, warfarin, heparin, minocycline, Vioxx, Celebrex, etc.; drugs which have an antineoplastic effect that are currently in Phase I, II and/or III trials; epothilones, analogs of epothilones, and their class of compounds; meiphalan (Alkeran), carmustine {BCNU} (BiCNU), busulfan (Busulfex), lomustine {CCNU} (CeeNU), cyclophosphamide (Cytoxan), dacarbazine (DTIC-Dome), polifeprosan 20 with carmustine implant (Giladel), sterile ifosfamide (Ifex), chlorambucil (Leuderan), mechlorethamine (Mustargen), busulfan (Myleran), cyclophosphamide (Neosar), carboplatin (Paraplatin), cisplatin (Platinol), thiotepa (Thioplex), capecitabine (Xeloda), streptozocin (Zanosar), bicalutamide (Casodex), flutamide (Eulexin), leuprolide acetate (Lupron), nilutamide (Nilandron), leuprolide acetate (Viadur), doxorubicin hydrochloride (Adriamycin), bleomycin sulfate (Blenoxane), daunorubicin hydrochloride (Cerubidine), dactinomycin (Cosmegen), daunorubicin citrate liposome injection (DaunoXome), doxorubicin hydrochloride liposome injection (Doxil), epirubicin hydrochloride (Ellence), idarubicin hydrochloride (Idamycin), mitomycin (Mutamycin) doxorubicin (Rubex), valrubicin (Valstar), anastrozole (Arimidex), toremifene citrate (nolvadex), fluorouracil (Adrucil), cytarabine (Cyttosar-U), fluorouracil (Efudex), fludarabine (Fludara), (Fluorouracil), floxuridine (FUDR), interferon alfa-2*b*, recombinant (Intron A), Immunex (Methotrexate), plicamycin (Mithracin), mercaptopurine (Purinethol), methotrexate (Rheumatrex), interferon alfa-2*a*, recombinant (Roferon-A (Thioguanine), medroxyprogersterone acetate (Depo-Provera), estramustine phosphate sodium (Emcyt), estradiol (Estrace), leuprolide acetate (Lupron), megestrol acetate (Megace), octreotide acetate (Sandostatin), octreotide acetate for injection suspension (Sandostatin LAR), diethylstilbestrol diphosphate (Stilphostrol), testolactone (Teslac), goserelin acetate (Zoladex), etoposide phosphate (Etopophos), vincristine sulfate (Oncovin), etoposide (Toposar), vinblastine (Velban), etoposide (VePesid), vincristine sulfate (Vincasar PFS), teniposide (Vumon), trastuzumab (Herceptin), gemtuzumab ozogamiem (Mylotarg), rituximab (Rituxan), exemestane (Aromasin), irinotecan hydrocholoride (Camptosar), asparaginase (Elspar), gemcitabine hydrochloride (Gemzar), altretamine (Hexalen), topotecan hydrochloride (Hycamtin), hydroxyurea (Hydrea), (Leucovorin calcium), cladribine (Leustatin), mitotate (Lysodren) procarbazine hydrochloride, (Matulane), vinorelbine tartrate (Navelbine), pentrostatin sodium (Nipent), mitoxantrone (Novantrone), pegaspargase (Oncaspar), denileukin diftitix (Ontak), altretinoin (Panretin), porfimer (Photofrin), bexarotene (Targretin, bexarotene (Targretin Gel), paclitaxel (Taxol), docetaxel (Taxotere), temozolomide (Temodar), bacillus of Calmette and Guerin (Theracys BCG Live), arsenic trioxide (Trisenox), tretinoin (Vesanoid); substances which foster anti-tumor activity; and all substances derived from and/or related to the foregoing substances.

4. A method for calculating a revised dose of a antineoplastic drug for a patient using said antineoplastic drug, comprising the steps of:

accepting as a first input the patient's current antineoplastic drug dose;

accepting as a second input the maximum dose of the antineoplastic drug;

accepting as a third input one or more numerical markers indicating a response of the patient to said antineoplastic drug; and calculating said revised dose, wherein said revised dose is a function of said current dose minus the ratio of the change in numerical markers and the ratio of said current dose to said maximum dose plus the percent of individual patient response multiplied by a response factor.

5. The method of claim 4, wherein:

said calculating step includes calculating said revised dose based on the equation $$RAD=CAD-\{[<(CANM-DANM)/CANM>/<1+(CAD/HIGH)>]\times CAD\}+LV$$

where:

$$LV=\{(RESP\times CAD)\times[(1+D)-(1+E)]/\text{abs }(1+D)\}/[1.3\char`\^(CAD/HIGH)]$$

$$E=CANM-PANM$$

$$D=DDNM-PDNM$$

$$RESP=RESPONSE/100$$

and wherein:

RAD=Revised Antineoplastic drug Dose
CAD=Current Antineoplastic drug Dose
CANM=Current Antineoplastic drug Numerical Marker
DANM=Desired Antineoplastic drug Numerical Marker
PANM=Previous Antineoplastic drug Numerical Marker
HIGH=The input parameter that is the high dose range for said antineoplastic drug
RESPONSE=Total dose available for individualizing patient dose
abs=The absolute value of
^=Raised to the $n^{th}$ power.

6. The method of claim 4, wherein:

said antineoplastic drug is selected from a group comprising: chemotherapeutic agents; drugs which have an antineoplastic effect, but which are not normally classified as chemotherapeutic agents including, warfarin, heparin, minocycline, Vioxx, Celebrex, etc.; drugs which have an antineoplastic effect that are currently in Phase I, II and/or III trials; epothilones, analogs of epothilones, and their class of compounds; melphalan (Alkeran), carmustine {BCNU} (BiCNU), busulfan (Busulfex), lomustine {CCNU} (CeeNU), cyclophosphamide (Cytoxan), dacarbazine (DTIC-Dome), polifeprosan 20 with carmustine implant (Giladel), sterile ifosfamide (Ifex), chlorambucil (Leuderan), mechlorethamine (Mustargen), busulfan (Myleran), cyclophosphamide (Neosar), carboplatin (Paraplatin), cisplatin (Platinol), thiotepa (Thioplex), capecitabine (Xeloda), streptozocin (Zanosar), bicalutamide (Casodex), flutamide (Eulexin), leuprolide acetate (Lupron), nilutamide (Nilandron), leuprolide acetate (Viadur), doxorubicin hydrochloride (Adriamycin), bleomycin sulfate (Blenoxane), daunorubicin hydrochloride (Cerubidine), dactinomycin (Cosmegen), daunorubicin citrate liposome injection (DaunoXome), doxorubicin hydrochloride liposome injection (Doxil), epirubicin hydrochloride (Ellence), idarubicin hydrochloride (Idamycin), mitomycin (Mutamycin) doxorubicin (Rubex), valrubicin (Valstar), anastrozole (Arimidex), toremifene citrate (nolvadex), fluorouracil (Adrucil), cytarabine (Cyttosar-U), fluorouracil (Efudex), fludarabine (Fludara), (Fluorouracil), floxuridine (FUDR), interferon alfa-2b, recombinant (Intron A), Immunex (Methotrexate), plicamycin (Mithracin), mercaptopurine (Purinethol), methotrexate (Rheumatrex), interferon alfa-2a, recombinant (Roferon-A (Thioguanine), medroxyprogersterone acetate (Depo-Provera), estramustine phosphate sodium (Emcyt), estradiol (Estrace), leuprolide acetate (Lupron), megestrol acetate (Megace), octreotide acetate (Sandostatin), octreotide acetate for injection suspension (Sandostatin LAR), diethylstilbestrol diphosphate (Stilphostrol), testolactone (Teslac), goserelin acetate (Zoladex), etoposide phosphate (Etopophos), vincristine sulfate (Oncovin), etoposide (Toposar), vinblastine (Velban), etoposide (VePesid), vincristine sulfate (Vincasar PFS), teniposide (Vumon), trastuzumab (Herceptin), gemtuzumab ozogamicin (Mylotarg), rituximab (Rituxan), exemestane (Aromasin), irinotecan hydrocholoride (Camptosar), asparaginase (Elspar), gemcitabine hydrochloride (Gemzar), altretamine (Hexalen), topotecan hydrochloride (Hycamtin), hydroxyurea (Hydrea), (Leucovorin calcium), cladribine (Leustatin), mitotate (Lysodren) procarbazine hydrochloride, (Matulane), vinorelbine tartrate (Navelbine), pentrostatin sodium (Nipent), mitoxantrone (Novantrone), pegaspargase (Oncaspar), denileukin diftitix (Ontak), altretinoin (Panretin), porfimer (Photofrin), bexarotene (Targretin, bexarotene (Targretin Gel), paclitaxel (Taxol), docetaxel (Taxotere), temozolomide (Temodar), bacillus of Calmette and Guerin (Theracys BCG Live), arsenic trioxide (Trisenox), tretinoin (Vesanoid); substances which foster anti-tumor activity; and all substances derived from and/or related to the foregoing substances.

7. A method for determining a dose of a antineoplastic drug for a patient, comprising the steps of:

administering an initial dose of said antineoplastic drug to the patient;

evaluating the patient to monitor and characterize one or more numerical surrogate markers used for monitoring said antineoplastic drug;

determining, based on said numerical surrogate markers, if a dose change for said antineoplastic drug is necessary; and calculating a revised dose as a function of said current dose minus the ratio of a percent response of the patient and the ratio of said current dose to said maximum dose plus the percent of individual patient response multiplied by a response factor.

8. The method of claim 7, wherein:

said antineoplastic drug is selected from a group comprising: chemotherapeutic agents; drugs which have an antineoplastic effect, but which are not normally classified as chemotherapeutic agents including, warfarin, heparin, minocycline, Vioxx, Celebrex, etc.; drugs which have an antineoplastic effect that are currently in Phase I, II and/or III trials; epothilones, analogs of epothilones, and their class of compounds; melphalan (Alkeran), carmustine {BCNU} (BiCNU), busulfan (Busulfex), lomustine {CCNU} (CeeNU), cyclophosphamide (Cytoxan), dacarbazine (DTIC-Dome), polifeprosan 20 with carmustine implant (Giladel), sterile ifosfamide (Ifex), chlorambucil (Leuderan), mechlorethamine (Mustargen), busulfan (Myleran), cyclophosphamide (Neosar), carboplatin (Paraplatin), cisplatin (Platinol), thiotepa (Thioplex), capecitabine (Xeloda), streptozocin (Zanosar), bicalutamide (Casodex), flutamide (Eulexin), leuprolide acetate (Lupron), nilutamide (Nilandron), leuprolide acetate (Viadur), doxorubicin hydrochloride (Adriamycin), bleomycin sulfate (Blenoxane), daunorubicin hydrochloride (Cerubidine), dactinomycin (Cosmegen), daunorubicin citrate liposome injection (DaunoXome), doxorubicin hydrochloride liposome injection (Doxil), epirubicin hydrochloride (Ellence), idarubicin hydrochloride (Idamycin), mitomycin (Mutamycin) doxorubicin (Rubex), valrubicin (Valstar), anastrozole (Arimidex), toremifene citrate (nolvadex), fluorouracil (Adrucil), cytarabine (Cyttosar-U), fluorouracil (Efudex), fludarabine (Fludara), (Fluorouracil), floxuridine (FUDR), interferon alfa-2b, recombinant (Intron A), Immunex (Methotrexate), plicamycin (Mithracin), mercaptopurine (Purinethol), methotrexate (Rheumatrex), interferon alfa-2a, recombinant (Roferon-A (Thioguanine), medroxyprogersterone acetate (Depo-Provera), estramustine phosphate sodium (Emcyt), estradiol (Estrace), leuprolide acetate (Lupron), megestrol acetate (Megace), octreotide acetate (Sandostatin), octreotide acetate for injection suspension (Sandostatin LAR), diethylstilbestrol diphosphate (Stilphostrol), testolactone (Teslac), goserelin acetate (Zoladex), etoposide phosphate (Etopophos), vincristine sulfate (Oncovin), etoposide (Toposar), vinblastine (Velban), etoposide (VePesid), vincristine sulfate (Vincasar PFS), teniposide (Vumon), trastuzumab (Herceptin), gemtuzumab ozogamicin (Mylotarg), rituximab (Rituxan), exemestane (Aromasin), irinotecan hydrocholoride (Camptosar), asparaginase (Elspar), gemcitabine hydrochloride (Gemzar), altretamine (Hexalen), topotecan hydrochloride (Hycamtin), hydroxyurea (Hydrea), (Leucovorin calcium), cladribine (Leustatin), mitotate (Lysodren) procarbazine hydrochloride, (Matulane), vinorelbine tartrate (Navelbine), pentrostatin sodium (Nipent), mitoxantrone (Novantrone), pegaspargase (Oncaspar), denileukin diftitix (Ontak), altretinoin (Panretin), porfimer (Photo fin), bexarotene (Targretin, bexarotene (Targretin Gel), paclitaxel (Taxol), docetaxel (Taxotere), temozolomide (Temodar), bacillus of Calmette and Guerin (Theracys BCG Live), arsenic trioxide (Trisenox), tretinoin (Vesanoid); substances which foster anti-tumor activity; and all substances derived from and/or related to the foregoing substances.

9. A method for determining a dose of an antineoplastic drug for a patient, comprising the steps of:

administering an initial dose of said antineoplastic drug to the patient;

examining the patient to monitor and characterize one or more numerical surrogate markers used for monitoring said antineoplastic drug;

determining if a dose change is necessary; and calculating a revised dose as a function of said current dose minus the ratio of the change in numerical markers and the ratio of said current dose to said maximum dose plus the percent of individual patient response multiplied by a response factor.

10. A method for calculating a revised dose of an antineoplastic drug for a patient, comprising the steps of:

accepting as input the patient's current antineoplastic drug dose;

accepting as input the maximum dose of the antineoplastic drug;

accepting as input the percent response of the patient based on surrogate markers for monitoring said antineoplastic drug; and calculating a revised dose, wherein said revised dose is a function of said current dose, said maximum dose, and said percent response of the patient based on said surrogate markers.

11. A method for calculating a revised dose of an antineoplastic drug for a patient, comprising the steps of:

accepting as input a patient's current antineoplastic drug dose;

accepting as input a maximum dose of the antineoplastic drug;

accepting as input the previous, current and desired values of one or more numerical markers indicating the response of the patient to said antineoplastic drug;

calculating a revised dose, wherein said revised dose is a function of said current dose, said maximum dose, and said previous, current and desired values of said numerical markers.

12. A storage device having stored thereon an ordered set of instructions which, when executed by a computer, performs a predetermined method, comprising:

first means for accepting as input a patient's current antineoplastic drug dose;

second means for accepting as input a maximum dose of the antineoplastic drug;

third means for accepting as input a percent response of a patient based on surrogate markers for monitoring said antineoplastic drug; and fourth means for calculating a revised dose, wherein said revised dose is a function of said current dose minus the ratio of a percent response of the patient and the ratio of said current dose to said maximum dose plus the percent of individual patient response multiplied by a response factor.

13. The storage device of claim 12, wherein:

said antineoplastic drug is selected from a group comprising: chemotherapeutic agents; drugs which have an antineoplastic effect, but which are not normally classified as chemotherapeutic agents including, warfarin, heparin, minocycline, Vioxx, Celebrex, etc.; drugs which have an antineoplastic effect that are currently in Phase I, II and/or III trials; epothilones, analogs of epothilones, and their class of compounds; meiphalan (Alkeran), carmustine {BCNU} (BiCNU), busulfan (Busulfex), lomustine {CCNU} (CeeNU), cyclophosphamide (Cytoxan), dacarbazine (DTIC-Dome), polifeprosan 20 with carmustine implant (Giladel), sterile ifosfamide (Ifex), chlorambucil (Leuderan), mechlorethamine (Mustargen), busulfan (Myleran), cyclophosphamide (Neosar), carboplatin (Paraplatin), cisplatin (Platinol), thiotepa (Thioplex), capecitabine (Xeloda), streptozocin (Zanosar), bicalutamide (Casodex), flutamide (Eulexin), leuprolide acetate (Lupron), nilutamide (Nilandron), leuprolide acetate (Viadur), doxorubicin hydrochloride (Adriamycin), bleomycin sulfate (Blenoxane), daunorubicin hydrochloride (Cerubidine), dactinomycin (Cosmegen), daunorubicin citrate liposome injection (DaunoXome), doxorubicin hydrochloride liposome injection (Doxil), epirubicin hydrochloride (Ellence), idarubicin hydrochloride (Idamycin), mitomycin (Mutamycin) doxorubicin (Rubex), valrubicin (Valstar), anastrozole (Arimidex), toremifene citrate (nolvadex), fluorouracil (Adrucil), cytarabine (Cyttosar-U), fluorouracil (Efudex), fludarabine (Fludara), (Fluorouracil), floxuridine (FUDR), interferon alfa-2$b$, recombinant (Intron A), Immunex (Methotrexate), plicamycin (Mithracin), mercaptopurine (Purinethol), methotrexate (Rheumatrex), interferon alfa-2$a$, recombinant (Roferon-A (Thioguanine), medroxyprogersterone acetate (Depo-Provera), estramustine phosphate sodium (Emcyt), estradiol (Estrace), leuprolide acetate (Lupron), megestrol acetate (Megace), octreotide acetate (Sandostatin), octreotide acetate for injection suspension (Sandostatin LAR), diethylstilbestrol diphosphate (Stilphostrol), testolactone (Teslac), goserelin acetate (Zoladex), etoposide phosphate (Etopophos), vincristine sulfate (Oncovin), etoposide (Toposar), vinblastine (Velban), etoposide (VePesid), vincristine sulfate (Vincasar PFS), teniposide (Vumon), trastuzumab (Herceptin), gemtuzumab ozogamicin (Mylotarg), rituximab (Rituxan), exemestane (Aromasin), irinotecan hydrocholoride (Camptosar), asparaginase (Elspar), gemcitabine hydrochloride (Gemzar), altretamine (Hexalen), topotecan hydrochloride (Hycamtin), hydroxyurea (Hydrea), (Leucovorin calcium), cladribine (Leustatin), mitotate (Lysodren) procarbazine hydrochloride, (Matulane), vinorelbine tartrate (Navelbine), pentrostatin sodium (Nipent), mitoxantrone (Novantrone), pegaspargase (Oncaspar), denileukin diftitix (Ontak), altretinoin (Panretin), porfimer (Photofrin), bexarotene (Targretin, bexarotene (Targretin Gel), paclitaxel (Taxol), docetaxel (Taxotere), temozolomide (Temodar), bacillus of Calmette and Guerin (Theracys BCG Live), arsenic trioxide (Trisenox), tretinoin (Vesanoid); substances which foster anti-tumor activity; and all substances derived from and/or related to the foregoing substances.

14. A storage device having stored thereon an ordered set of instructions which, when executed by a computer, performs a predetermined method, comprising:

first means for accepting as input the patient's current antineoplastic drug dose;

second means for accepting as input the maximum dose of the antineoplastic drug;

third means for accepting as input one or more numerical markers indicating the response of the patient to said antineoplastic drug; and fourth means for calculating a revised dose, wherein said revised dose is a function of said current dose minus the ratio of the change in numerical markers and the ratio of said current dose to said maximum dose plus the percent of individual patient response multiplied by a response factor.

15. An apparatus for calculating a revised dose of an antineoplastic drug for a patient, comprising:

first means for accepting as input one or more markers which indicate a patient's response to a dose of said antineoplastic drug;

second means for accepting as input the patient's current antineoplastic drug dose;

third means for accepting as input the maximum dose of the antineoplastic drug; and fourth means for calculating a revised dose of the antineoplastic drug as a function of said markers, said current antineoplastic drug dose, and said maximum antineoplastic drug dose.

16. The apparatus of claim 15, wherein:

said markers are actual numerical markers.

17. The apparatus of claim 15, wherein:

said markers are surrogate markers representing a percent response of the patient to the antineoplastic drug.

18. The apparatus of claim 15, wherein:

said revised dose is calculated by the following equation:

$$RAD=CAD-\{[<(CANM-DANM)/CANM>/<1+(CAD/HIGH)>]\times CAD\}+LV$$

where:

$$LV=\{(RESP\times CAD)\times[(1+D)-(1+E)]/\text{abs }(1+D)\}/[1.3\hat{}(CAD/HIGH)]$$

$$E=CANM-PANM$$

$$D=DDNM-PDNM$$

$$RESP=RESPONSE/100,$$

and wherein:

RAD=Revised Antineoplastic drug Dose

CAD=Current Antineoplastic drug Dose

CANM=Current Antineoplastic drug Numerical Marker

DANM=Desired Antineoplastic drug Numerical Marker

PANM=Previous Antineoplastic drug Numerical Marker

HIGH=The input Parameter that is the high dose range for said antineoplastic drug RESPONSE=Total dose available for individualizing patient dose abs=The absolute value of ^=Raised to the nth power.

19. The apparatus of claim 15, wherein:

said revised dose is calculated by the equation:

$$RAD=CAD-\{[<(SMP-100)/SMP>/<1+(CAD/HIGH)>]\times CAD\}+LV$$

where:

$$LV = \{(RESP \times CAD) \times [(100 - RES) \times 0.01]\} / [1.3\hat{\ }(CAD/HIGH)]$$

RESP=RESPONSE/100 and wherein:
RAD=Revised Antineoplastic drug Dose
CAD=Current Antineoplastic drug Dose
SMP=Surrogate Marker Percent response of patient
RES=Percent response of patient to last dosing based on surrogate marker
HIGH=The input parameter that is the high dose range for said antineoplastic drug
RESPONSE=Total dose available for individualizing patient dose
abs=The absolute value of
^=Raised to the nth power.

20. The apparatus of claim 15, wherein:
said antineoplastic drug is selected from a group comprising: chemotherapeutic agents; drugs which have an antineoplastic effect, but which are not normally classified as chemotherapeutic agents including, warfarin, heparin, minocycline, Vioxx, Celebrex, etc.; drugs which have an antineoplastic effect that are currently in Phase I, II and/or III trials; epothilones, analogs of epothilones, and their class of compounds; meiphalan (Alkeran), carmustine {BCNU} (BiCNU), busulfan (Busulfex), lomustine {CCNU} (CeeNU), cyclophosphamide (Cytoxan), dacarbazine (DTIC-Dome), polifeprosan 20 with carmustine implant (Giladel), sterile ifosfamide (Ifex), chlorambucil (Leuderan), mechlorethamine (Mustargen), busulfan (Myleran), cyclophosphamide (Neosar), carboplatin (Paraplatin), cisplatin (Platinol), thiotepa (Thioplex), capecitabine (Xeloda), streptozocin (Zanosar), bicalutamide (Casodex), flutamide (Eulexin), leuprolide acetate (Lupron), nilutamide (Nilandron), leuprolide acetate (Viadur), doxorubicin hydrochloride (Adriamycin), bleomycin sulfate (Blenoxane), daunorubicin hydrochloride (Cerubidine), dactinomycin (Cosmegen), daunorubicin citrate liposome injection (DaunoXome), doxorubicin hydrochloride liposome injection (Doxil), epirubicin hydrochloride (Ellence), idarubicin hydrochloride (Idamycin), mitomycin (Mutamycin) doxorubicin (Rubex), valrubicin (Valstar), anastrozole (Arimidex), toremifene citrate (nolvadex), fluorouracil (Adrucil), cytarabine (Cyttosar-U), fluorouracil (Efudex), fludarabine (Fludara), (Fluorouracil), floxuridine (FUDR), interferon alfa-2$b$, recombinant (Intron A), Immunex (Methotrexate), plicamycin (Mithracin), mercaptopurine (Purinethol), methotrexate (Rheumatrex), interferon alfa-2$a$, recombinant (Roferon-A (Thioguanine), medroxyprogesterone acetate (Depo-Provera), estramustine phosphate sodium (Emcyt), estradiol (Estrace), leuprolide acetate (Lupron), megestrol acetate (Megace), octreotide acetate (Sandostatin), octreotide acetate for injection suspension (Sandostatin LAR), diethylstilbestrol diphosphate (Stilphostrol), testolactone (Teslac), goserelin acetate (Zoladex), etoposide phosphate (Etopophos), vincristine sulfate (Oncovin), etoposide (Toposar), vinblastine (Velban), etoposide (VePesid), vincristine sulfate (Vincasar PFS), teniposide (Vumon), trastuzumab (Herceptin), gemtuzumab ozogamicin (Mylotarg), rituximab (Rituxan), exemestane (Aromasin), irinotecan hydrocholoride (Camptosar), asparaginase (Elspar), gemcitabine hydrochloride (Gemzar), altretamine (Hexalen), topotecan hydrochloride (Hycamtin), hydroxyurea (Hydrea), (Leucovorin calcium), cladribine (Leustatin), mitotate (Lysodren) procarbazine hydrochloride, (Matulane), vinorelbine tartrate (Navelbine), pentrostatin sodium (Nipent), mitoxantrone (Novantrone), pegaspargase (Oncaspar), denileukin diftitix (Ontak), altretinoin (Panretin), porfimer (Photofrin), bexarotene (Targretin, bexarotene (Targretin Gel), paclitaxel (Taxol), docetaxel (Taxotere), temozolomide (Temodar), bacillus of Calmette and Guerin (Theracys BCG Live), arsenic trioxide (Trisenox), tretinoin (Vesanoid); substances which foster anti-tumor activity; and all substances derived from and/or related to the foregoing substances.

* * * * *

UNITED STATES PATENT AND TRADEMARK OFFICE
CERTIFICATE OF CORRECTION

PATENT NO. : 6,581,606 B2
DATED : June 24, 2003
INVENTOR(S) : John D. Kutzko

It is certified that error appears in the above-identified patent and that said Letters Patent is hereby corrected as shown below:

Title page,
Item [56], References Cited, U.S. PATENT DOCUMENTS, insert:
-- 5,365,948    11/1994    McMichael    128/898
   5,542,436    8/1996     McMichael    128/897
   5,694,950    12/1997    McMichael    128/898 --

Column 8,
Line 40, replace "meiphalan" with -- melphalan --.

Column 15,
Line 28, replace "meiphalan" with -- melphalan --.

Signed and Sealed this

Twentieth Day of January, 2004

JON W. DUDAS
*Acting Director of the United States Patent and Trademark Office*